United States Patent
Kim et al.

(10) Patent No.: US 9,587,087 B2
(45) Date of Patent: *Mar. 7, 2017

(54) METHOD FOR PREPARING ESTER COMPOSITION AND RESIN COMPOSITION

(71) Applicant: LG Chem, Ltd., Seoul (KR)

(72) Inventors: Hyun Kyu Kim, Daejeon (KR); Da Won Jung, Daejeon (KR); Mi Yeon Lee, Daejeon (KR); Dong Hyun Ko, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/314,761

(22) Filed: Jun. 25, 2014

(65) Prior Publication Data

US 2014/0336294 A1    Nov. 13, 2014

Related U.S. Application Data

(63) Continuation of application No. PCT/KR2013/005920, filed on Jul. 3, 2013.

(30) Foreign Application Priority Data

| May 8, 2013 | (KR) | 10-2013-0051617 |
| Jun. 14, 2013 | (KR) | 10-2013-0068289 |

(51) Int. Cl.
| C08K 5/12 | (2006.01) |
| C07C 69/82 | (2006.01) |
| C07C 67/08 | (2006.01) |

(52) U.S. Cl.
CPC .............. *C08K 5/12* (2013.01); *C07C 67/08* (2013.01)

(58) Field of Classification Search
CPC ............ C07C 67/08; C07C 67/50; C08K 5/10
USPC .............................................. 560/64; 524/314
See application file for complete search history.

(56) References Cited

U.S. PATENT DOCUMENTS

| 7,361,779 B1 | 4/2008 | Holt et al. | |
| 7,732,634 B2 * | 6/2010 | Soled et al. | 562/509 |
| 9,062,179 B2 * | 6/2015 | Kim et al. | |
| 2007/0037926 A1 | 2/2007 | Olsen et al. | |
| 2008/0057317 A1 | 3/2008 | Kettner et al. | |
| 2008/0183012 A1* | 7/2008 | Cook et al. | 562/480 |
| 2012/0006462 A1 | 1/2012 | Boquillon | |

FOREIGN PATENT DOCUMENTS

| GB | 1468563 | * | 3/1997 |
| JP | 2001-31794 A | | 2/2001 |
| JP | 02001031794 A | * | 2/2001 |
| JP | 2010525100 | | 7/2010 |
| JP | 2012184529 A | | 9/2012 |
| KR | 20080034920 A | | 4/2008 |
| KR | 1020130035493 | | 4/2013 |
| WO | 2010071717 A1 | | 6/2010 |

OTHER PUBLICATIONS

"Chemical Technology", by Zhu Shiqing et al., p. 225, Chemical Industry Press.
Practical Handbook of Polymer Anti-aging, Research Institute of Synthetic Material, Ministry of Chemical Industry, Jinhai Chemical Co. LTD., Jun. 30, 1999, p. 198, Chemical Industry Press.

* cited by examiner

*Primary Examiner* — Tae H Yoon
(74) *Attorney, Agent, or Firm* — Dentons US LLP

(57) ABSTRACT

Disclosed are a method for preparing an ester composition and a resin composition comprising the ester composition. It is possible to suitably prepare a plasticizer composition which improves processability due to high absorption rate and short fusion time to resins and thus provides superior physical properties when processed with resins.

6 Claims, 2 Drawing Sheets

METHOD FOR PREPARING ESTER COMPOSITION AND RESIN COMPOSITION

This application is a Continuation Bypass of International Application PCT/KR2013/005920, with an international filing date of Jul. 3, 2013 which claims priority to and the benefit of Korean Patent Application No. 10-2013-0051617, filed on May 8, 2013, and Korean Patent Application No. 10-2013-0068289, filed on Jun. 14, 2013, all of which are incorporated herein by reference in their entirety.

TECHNICAL FIELD

The present invention relates to a method for preparing an ester composition and a resin composition. More specifically, the present invention relates to a method for suitably preparing a plasticizer composition which has improved processability due to high absorption rate and short fusion time to resins and thus provides superior physical properties when processed with resins.

BACKGROUND ART

In general, a plasticizer is composed of an ester produced by reaction of an alcohol with polycarboxylic acid such as phthalic acid or adipic acid. Examples of commercially essential plasticizers include: adipates of C8, C9 and C10 alcohols, for example di(2-ethyl hexyl)adipate, diisononyl adipate and diisodecyl adipate; and phthalates of C8, C9 and C10 alcohols, for example, di(2-ethyl hexyl)phthalate, diisononyl phthalate and diisodecyl phthalate.

Specifically, the di(2-ethyl hexyl)phthalate is incorporated in toys, films, shoes, coatings, flooring materials, gloves, wallpaper, artificial leather, sealants, tarpaulin, car floor coatings, furniture, foam mats and acoustic insulation panels via plastisol and dry mixing. This is also used for production of exterior and insulating materials for PVC cables, and other calendered plastic PVC products.

Di(2-ethyl hexyl)adipate is predominantly primarily used for films and is used at a low level for other products such as wallpaper, artificial leather, car floor coatings, gloves and sealants. In particular, di(2-ethyl hexyl)adipate is predominantly used when products are used at a low temperature and/or plastisol is used as a process intermediate.

Apart from di(2-ethyl hexyl)adipate, a great deal of research associated with eco-friendly plasticizers continues due to environmental problems associated with phthalate-based plasticizers.

DISCLOSURE

Technical Problem

During repeated research into eco-friendly plasticizers, the present inventors discovered that an ester composition comprising a specific content of hybrid branched type alkyl-substituted terephthalate compound, among hybrid branched type, non-hybrid unbranched type and non-hybrid branched type alkyl-substituted terephthalate compounds, has improved processability due to high absorption rate and short fusion time to resins, and provides superior physical properties during sheet formulation and compound formulation of wires, automobile interior materials, films, sheets, tubes, wallpaper, toys, floor materials and the like. The present invention has been completed, based on this discovery.

That is, it is one object of the present invention to provide a method for preparing an ester composition comprising hybrid branched type, non-hybrid unbranched type and non-hybrid branched type alkyl-substituted terephthalate compounds as eco-friendly plasticizers, wherein the hybrid branched type alkyl-substituted terephthalate compound is present in a specific amount in the ester composition.

It is another object of the present invention to provide a resin composition comprising the ester composition.

Technical Solution

In accordance with one aspect of the present invention, the above and other objects can be accomplished by the provision of a method for preparing an ester composition comprising hybrid branched type, non-hybrid unbranched type and non-hybrid branched type alkyl-substituted terephthalate compounds through esterification reaction, wherein the hybrid branched type alkyl-substituted terephthalate compound is present in an amount of 1 to 70% by weight.

In another aspect of the present invention, provided is a resin composition comprising the ester composition prepared by the method and a resin.

Hereinafter, the present invention will be described in detail.

That is, the present invention is characterized in that an ester composition comprising hybrid branched type, non-hybrid unbranched type and non-hybrid branched type alkyl-substituted terephthalate compounds is prepared wherein the hybrid branched type alkyl-substituted terephthalate compound is present in a specific amount in the ester composition.

As used herein, the term "hybrid branched type" refers to a structure in which alkyl groups substituted at symmetric positions in a phenyl group are different and a kind of branched chain is contained, unless specified otherwise.

In addition, as used herein, the term "non-hybrid unbranched type" refers to a structure in which alkyl groups substituted at symmetric positions in a phenyl group are identical and two kinds of linear hydrocarbons are contained without a branched chain, unless specified otherwise.

Furthermore, as used herein, the term "non-hybrid branched type" refers to a structure in which alkyl groups substituted at symmetric positions in a phenyl group are identical and two kinds of branched chains are contained, unless specified otherwise.

According to the present invention, for example, among hybrid branched type, non-hybrid unbranched type and non-hybrid branched type alkyl-substituted terephthalate compounds obtained by esterification using an acid catalyst, the hybrid branched type alkyl-substituted terephthalate compound is present in an amount of 1 to 70% by weight, 5 to 50% by weight, 10 to 50% by weight, 20 to 50% by weight, or 25 to 50% by weight. The content range can be accomplished by controlling esterification reaction conditions.

The substituted-alkyl is for example an alkyl group having 3 to 10 carbon atoms. In another example, the substituted-alkyl comprises at least one independently selected from an alkyl group having 3 to 4 carbon atoms and an alkyl group having 8 to 10 carbon atoms in consideration of process easiness (plasticization efficiency) caused by high absorption rate to resins and migration loss level.

In another example, the hybrid branched type alkyl-substituted terephthalate compound may be represented by the following Formula 1.

[Formula 1]

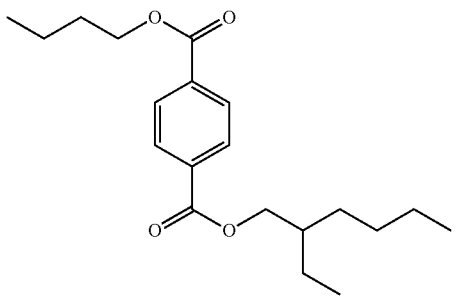

In another example, the non-hybrid unbranched type alkyl-substituted terephthalate compound may be represented by the following Formula 2.

[Formula 2]

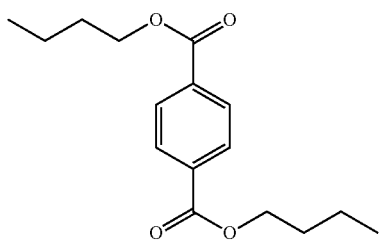

In another example, the non-hybrid branched type alkyl-substituted terephthalate compound may be represented by the following Formula 3.

[Formula 3]

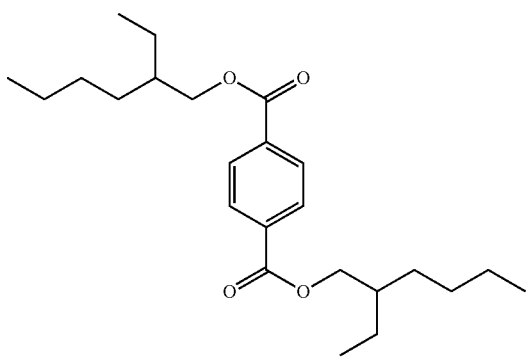

In another example, a mix ratio of the non-hybrid unbranched type alkyl-substituted terephthalate compound to the non-hybrid branched type alkyl-substituted terephthalate compound is a weight ratio of 1:99 to 40:60, 1:99 to 15:85, 1:99 to 9.9:90.1 or 1:99 to 9.6:90.4. Within this range, processability such as absorption rate and fusion time, and other physical properties can be improved.

Esterification conditions that satisfy these requirements are for example accomplished by mixing an unbranched alcohol with a branched alcohol.

In a specific example, the unbranched alcohol is an unbranched aliphatic alcohol having a C3-C4 alkyl group and is present in an amount of 1 to 80% by weight, or 15 to 50% by weight, with respect to 100% by weight of the alcohol. In another example, the unbranched alcohol may be n-butyl alcohol.

In addition, in a specific example, the branched alcohol may be a branched aliphatic alcohol having a C8-C10 alkyl group and may be present in an amount of 99 to 20% by weight, or 80 to 20% by weight, with respect to 100% by weight of the alcohol. In another example, the branched alcohol is 2-ethyl hexanol.

In addition, esterification reaction conditions that satisfy these requirements for example include using terephthalic acid having a mean particle diameter of 30 to 100 μm, or 39 to 91 μm. Within this range, reaction time is reduced and production efficiency can thus be improved.

In a specific example, the terephthalic acid may be mixed with an alcohol after being ground to the particle diameter defined above, or ground to the particle diameter after being mixed with the alcohol.

The grinding may be selected from dry grinding and wet grinding, if necessary. In a specific example, a high-speed rotation wet grinder such as a Cavitron or homogenizer may be used.

In another example, the high-speed rotation may be 3,000 to 50,000 rpm, or 10,000 to 50,000 rpm, so that the desired mean particle diameter distribution can be obtained within a short time.

Contents of the terephthalic acid and the alcohol may be within 10 to 40 mol % and 90 to 60 mol %, 20 to 30 mol % and 80 to 70 mol %, or 21 to 29 mol % and 79 to 71 mol %, respectively, with respect to the total moles of all reactants. For reference, within this range, reactant concentration of esterification, which is a reversible reaction, is increased, reverse reaction is inhibited and reaction rate can thus be increased.

If necessary, carboxylic acid, polycarboxylic acid or an anhydride thereof may be further added.

Esterification reaction conditions that satisfy these requirements for example include using a metal alkoxide compound or an acid catalyst as a reaction catalyst at a reaction temperature of 130 to 250° C., 130 to 220° C., or 180 to 220° C., for a reaction time of 1 to 10 hours, or 5 to 7 hours.

The metal alkoxide compound comprises for example at least one selected from titanium tetraalkoxide [Ti(OR)$_4$] such as tetraisobutyl titanate or tetraisopropyl titanate, and tin dialkoxide [Sn(OR)$_2$] such as dibutyl tin oxide.

The acid catalyst comprises for example at least one selected from paratoluenesulfonic acid, methanesulfonic acid, ethanesulfonic acid, propanesulfonic acid and sulfuric acid.

The reaction catalyst may be present at 0.1 to 15 parts by weight, 0.1 to 10 parts by weight, 0.1 to 7 parts by weight, or 0.1 to 5.0 parts by weight, with respect to 100 parts by weight of terephthalic acid as a reaction raw material. For reference, when the content of reaction catalyst is lower than the range defined above, reaction efficiency may be deteriorated, and when the content of reaction catalyst is higher than the range defined above, products may be discolored.

The esterification reaction may be carried out under a nitrogen atmosphere in order to block exterior air of a reaction system and nitrogen may be bubbled into the reaction solution in order to remove water produced during reaction due to condensation of esterification. In order to accomplish this object or other objects, the esterification reaction may be carried out under an increased or reduced pressure.

The plasticizer composition, that is, the ester composition, can be obtained at a purity of 96 to 99.99%, or 96.1 to 99.1% through common post-treatment processes such as neutralization, washing with water and dealcoholization.

The ester composition comprises a mixture of hybrid branched type, non-hybrid unbranched type and non-hybrid branched type alkyl-substituted terephthalate compounds, wherein the hybrid branched type alkyl-substituted terephthalate compound is present in an amount of 1 to 20% by weight, 1 to 19.5% by weight, 1 to 19% by weight, or 5 to 12% by weight. Within this range, there is an effect of superior processability.

A resin composition can be provided by mixing the ester composition with a resin. The resin is for example a thermoplastic resin and, in another example, comprises at least one selected from ethylene vinyl acetate, polyethylene, polypropylene, polyvinyl chloride, poly styrene, polyurethane, thermoplastic elastomers and polylactic acid.

The resin composition for example has an absorption rate of plasticizer of 1 to 10 minutes, 3 to 8 minutes, or 4 to minutes. Within this range, there are effects of superior workability and processability.

The absorption rate of the present invention is evaluated by measuring a time until which the resin is mixed with the plasticizer under mixing conditions of 77° C. at 66 rpm, 400 g of PVC (product name: LS100, produced by LG Chem. Ltd.) and 200 g of a plasticizer using a mixer (product name: Brabender, P600) and torque of the mixer is then stabilized.

Stabilization of the torque means that a torque peak maintains flatness after it increases and then gradually decreases, when the resin is first added and the plasticizer is then added thereto in order to measure absorption rate. This state can be seen by a graph on a monitor.

In addition, the resin composition has a sol viscosity of 4,000 to 15,000 cp, 5,000 to 11,000 cp, or 6,000 to 9,000 cp. Within this range, there is an effect of securing stable processability.

The sol viscosity of the present invention is measured using a Brookfield (LV type) viscosity meter, a #4 spindle is used and the measurement is carried out at 6 rpm and 12 rpm. 100 phr of PVC as a sample (PB900, LG Chem. Ltd.), 75 phr of a plasticizer, 4 phr of a stabilizing agent (KSZ111XF), 3 phr of a foaming agent (W1039), 13 phr of $TiO_2$ (TMCA100), 130 phr of $CaCO_3$ (OMYA10), 10 phr of a viscosity depressant (Exa-sol) and 1 phr of a dispersant (BYK3160) were mixed to prepare plastisol and the plastisol was stored at 25° C. for 1 hour and a sol viscosity thereof was then measured.

The resin composition may contain a low content of viscosity depressant, as compared to conventional products, or does not contain a viscosity depressant, that is, is a viscosity depressant-free resin composition.

The viscosity depressant-free composition of the present invention means a composition which does not contain at all a viscosity depressant to control viscosity of the resin composition.

The ester composition may be mixed in an amount of 5 to 150 parts by weight, or 5 to 100 parts by weight, with respect to 100 parts by weight of the resin. In addition, at least one plasticizer composition selected from dioctyl phthalate (DOP), dibutyl phthalate (DBP), dioctyl terephthalate (DOTP), diisononyl phthalate (DINP) and diisodecyl phthalate (DIDP) may be further added in an amount of 5 to 150 parts by weight, or 5 to 100 parts by weight, with respect to 100 parts by weight of the resin.

Furthermore, the resin composition may further comprise 0.5 to 7 parts by weight of a stabilizing agent, 0.5 to 3 parts by weight of a lubricant or the like, and may optionally further comprise at least one common additive.

In addition, the resin composition may for example further comprise a filler.

Any filler may be used without particular limitation so long as it is commonly used in the technical field to which the resin composition of the present invention pertains.

The filler may for example be added in an amount of 10 to 300 parts by weight, 50 to 200 parts by weight, or 100 to 200 parts by weight, with respect to 100 parts by weight of the resin.

In addition, the resin composition may for example further comprise at least one selected from the group consisting of a pigment, a dye, a processing aid, a dispersant, a foaming agent, an antifoaming agent and a viscosity depressant.

Each of the pigment, dye, processing aid, dispersant, foaming agent, antifoaming agent and viscosity depressant is present in, for example, 0.1 to 20 parts by weight, or 1 to 15 parts by weight, based on 100 parts by weight of the resin.

The resin composition may for example be used for manufacture of sheet formulation and compound formulation products such as cables, automobile interior materials, films, sheets, tubes, wallpaper, toys and floor materials.

Advantageous Effects

The present invention provides appropriate preparation of a plasticizer composition which has a high absorption rate and a short fusion time to resins and provides improvement in processability.

BEST MODE

Figure 1:
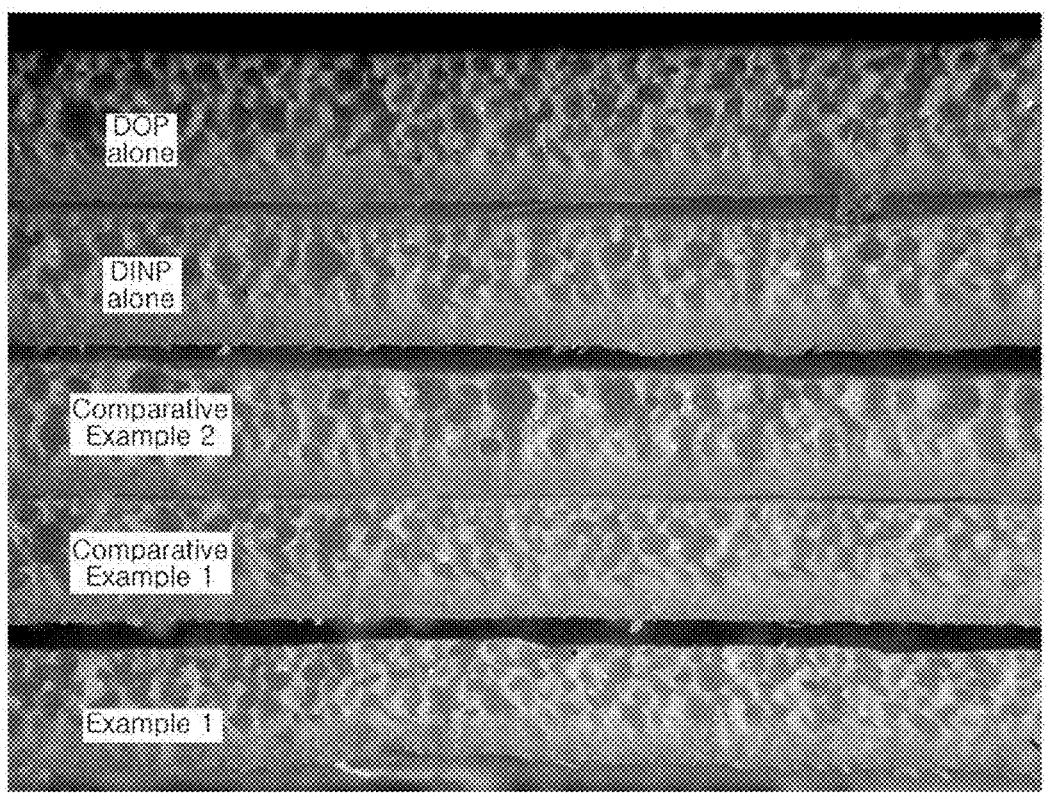
FIG. 1 shows an optical microscope image (×50) of Example 1 according to the present invention, Comparative Examples 1 and 2, dioctyl phthalate (DOP) alone and diisononyl phthalate (DINP) alone, and DOP alone, DINP alone, Comparative Example 2, Comparative Example 1 and Example 1 are represented in FIG. 1 from the top to the bottom in this order.

Now, the present invention will be described in more detail with reference to the following examples. These examples are provided only to illustrate the present invention.

Example 1

Terephthalic acid was ground using a Cavitron to prepare a ground terephthalic acid having a mean particle diameter (measured with a laser scattering analyzer, Nicomp 380) of 30 to 100 μm. 440 g of the ground terephthalic acid, 302 g of n-butanol and 530 g of 2-ethyl hexanol were subjected to esterification reaction in the presence of 32 g of 70% methane sulfonic acid at 130° C. for 7 hours. The reaction product was neutralized with $Na_2CO_3$, washed with water once and dealcoholized by heating under reduced pressure to obtain a plasticizer composition.

As a result of analysis of the obtained plasticizer composition using a GC-mass spectrometer (product name: Agilent 7890 GC, column: HP-5, carrier gas: helium. maintenance at initial temperature of 70° C. for 3 minutes and a temperature is elevated to 280° C. at a rate of 10° C./min and maintenance for 5 minutes), the plasticizer composition comprised substances having the following Formulas 1, 2 and 3.

[Formula 1]

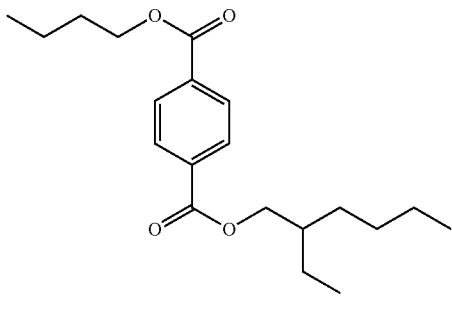

[Formula 2]

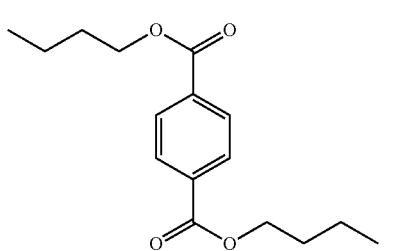

[Formula 3]

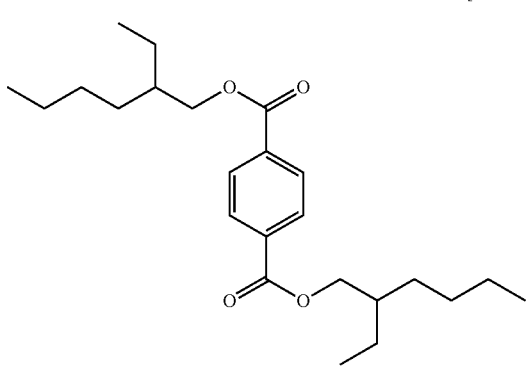

It can be seen that a weight ratio of the Formula 1, Formula 2 and Formula 3 was 50:10:40.

Example 2

A plasticizer composition was prepared by repeating the same process as in Example 1, except that 440 g of terephthalic acid ground in the same manner as in Example 1, 98 g of n-butanol and 823 g of 2-ethyl hexanol were reacted in the presence of 32 g of 70% methane sulfonic acid at 140° C. for 6 hours. In addition, as a result of GC-mass spectrometry, it was seen that a weight ratio of Formula 1, Formula 2 and Formula 3 was 25:3:72.

Example 3

A plasticizer composition was prepared by repeating the same process as in Example 1, except that 440 g of terephthalic acid ground in the same manner as in Example 1, 49 g of n-butanol and 909 g of 2-ethyl hexanol were reacted in the presence of 32 g of 70% methane sulfonic acid at 140° C. for 6 hours. In addition, as a result of GC-mass spectrometry, it was seen that a weight ratio of Formula 1, Formula 2 and Formula 3 was 12:2:86.

Example 4

A plasticizer composition was prepared by repeating the same process as in Example 1, except that 440 g of terephthalic acid ground in the same manner as in Example 1, 25 g of n-butanol and 951 g of 2-ethyl hexanol were reacted in the presence of 32 g of 70% methane sulfonic acid at 140° C. for 6 hours. In addition, as a result of GC-mass spectrometry, it was seen that a weight ratio of Formula 1, Formula 2 and Formula 3 was 5:1:94.

Comparative Example 1

A plasticizer was prepared by repeating the same process as in Example 1, except that 440 g of terephthalic acid was reacted with 890 g of n-butanol at 130° C. for 13 hours. In addition, as a result of GC-mass spectrometry of the obtained plasticizer, a compound of Formula 2 was identified.

[Formula 2]

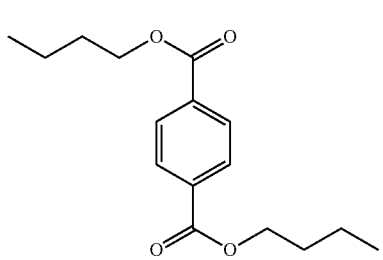

Comparative Example 2

A plasticizer composition was prepared by repeating the same process as in Example 1, except that 440 g of terephthalic acid was reacted with 1,060 g of 2-ethyl hexanol using 1.6 g of tetraisopropyl titanate as a catalyst at 220° C. for 5 hours.

In addition, as a result of GC-mass spectrometry of the obtained plasticizer, a compound of Formula 3 was identified.

[Formula 3]

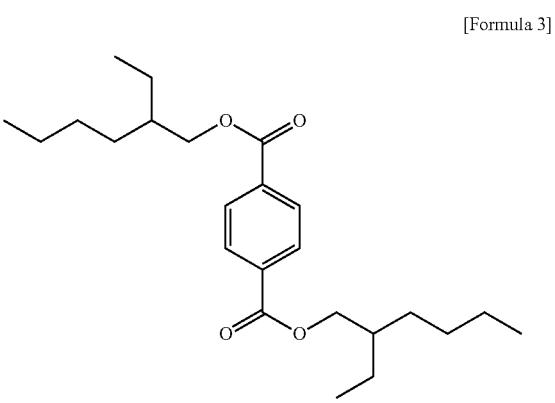 [SMILES: CCCCC(CC)COC(=O)c1ccc(C(=O)OCC(CC)CCCC)cc1]

Application Example 5 to 100 parts by weight of plasticizers obtained in Examples 1 to 4 and Comparative Examples 1 and 2, DOP alone and DINP alone were added to 100 parts by weight of a vinyl chloride resin, and a stabilizing agent, a lubricant and a foaming agent were added thereto, followed by extrusion. Physical properties such as absorption rate and processability were evaluated.

As an absorption rate (fusion test) of Example 1, a mixing time measured under conditions of 77° C., 60 rpm/PVC (product name: LS 100) 400 g and plasticizer 200 g was 244 seconds, which was superior to the case (306 seconds) in which dioctyl phthalate (DOP) was used alone, and was considerably superior to the case (428 seconds) in which dioctyl terephthalate (DOTP) was used alone (Comparative Example 2). As a result of the melting test of Example 1, melting time was 32 seconds.

In addition, regarding a migration resistance of Example 1, a migration loss calculated as a level of plasticizer lost by migration after heating at 80° C. for 72 hours was 3.75%.

In addition, processing properties of wallpaper were evaluated. As can be seen from FIG. 1, foamability of wallpaper produced using the sample of Example 1 was uniform in view of size, shape and arrangement of cells, as compared to the case in which dioctyl phthalate (DOP) alone, diisononyl phthalate (DINP) alone or dioctyl terephthalate (DOTP) alone was used, when a state of cells after foaming was measured with an optical microscope.

As an absorption rate (fusion test) of Example 2, a mixing time measured under conditions of 77° C., 60 rpm/PVC (product name: LS 100) 400 g and plasticizer 200 g was 280 seconds, which was superior to the case (306 seconds) in which dioctyl phthalate (DOP) was used alone, and like Example 1, was considerably superior to the case (Comparative Example 2) in which dioctyl terephthalate (DOTP) of was used alone. As a result of the melting test of Example 2, melting time was 38 seconds. As a result of migration resistance, resistance was 3.46%.

In addition, processing properties of wallpaper were evaluated. As can be seen from FIG. 2, foamability of wallpaper produced using the sample of Example 2 was uniform in view of size, shape and arrangement of cells, as compared to the case in which dioctyl phthalate (DOP) alone, diisononyl phthalate (DINP) alone or dioctyl terephthalate (DOTP) alone was used, when a state of cells after foaming was measured with an optical microscope.

As an absorption rate (fusion test) of Comparative Example 1, a mixing time measured under the conditions of 77° C., 60 rpm/PVC (product name: LS 100) 400 g, and plasticizer 200 g was 100 seconds, which was considerably low, as compared to the case (306 seconds) in which dioctyl phthalate (DOP) was used alone.

In addition, as a migration resistance of Comparative Example 1, a migration loss calculated as a level of plasticizer lost by migration after heating at 80° C. for 72 hours was 10.56% which was higher than the case (3.95%) in which DOP was used alone. This indicates that the product of Comparative Example 1 was increased in migration due to low molecular weight and disadvantageous structure as compared to DOP. Comparative Example 2 had a migration loss of 3.54%.

Figure 2:
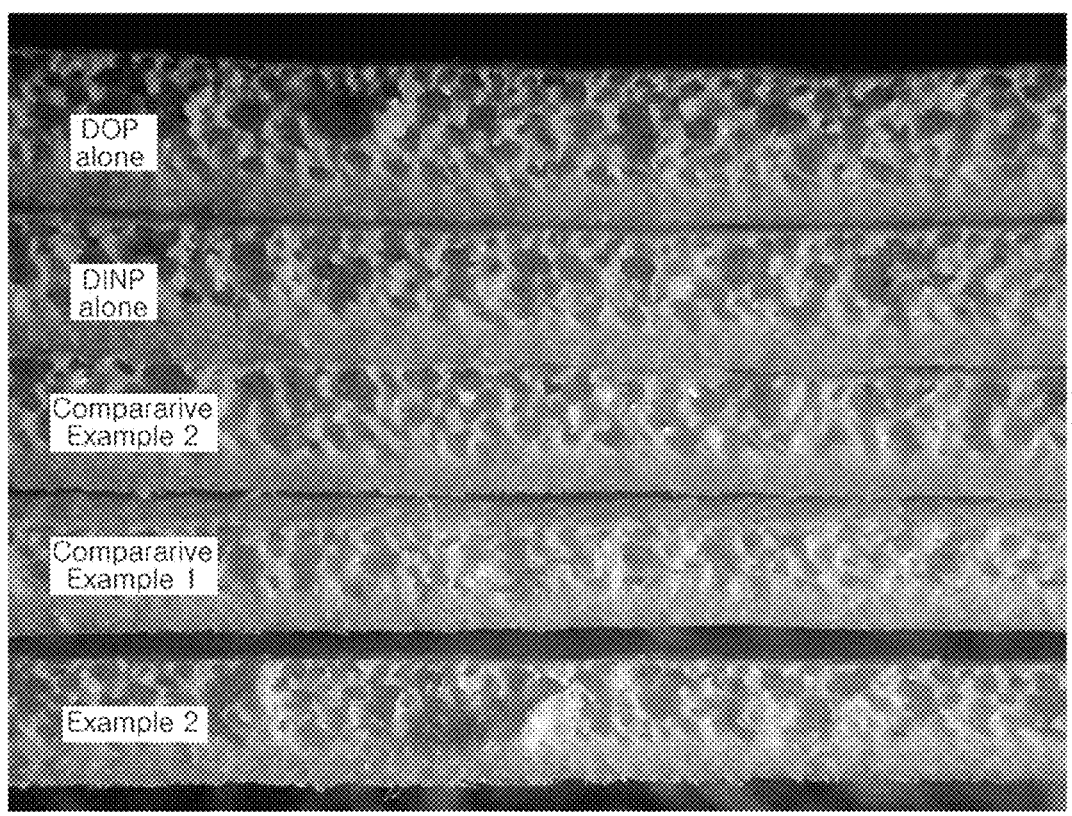
FIG. 2 shows an optical microscope image (×50) of Example 2 according to the present invention, Comparative Examples 1 and 2, dioctyl phthalate (DOP) alone and diisononyl phthalate (DINP) alone, and DOP alone, DINP alone, Comparative Example 2, Comparative Example 1 and Example 2 are represented in FIG. 2 from the top to the bottom in this order.

Furthermore, as can be seen from FIGS. 1 and 2, foamability of wallpaper produced using the sample of Comparative Example 1 was uniform in view of size, shape and arrangement of cells after foaming, as compared to the case in which DOP, DINP or DOTP was used alone. As a result of the fusion test of Comparative Example 2, melting time was 138 seconds, and as a result of measurement of migration resistance, migration was 3.54%.

Measured values are summarized in the following Table 1.

TABLE 1

| Items | DOP alone | DINP alone | Comp. Ex. 2 | Comp. Ex. 1 | Ex. 1 | Ex. 2 | Ex. 3 | Ex. 4 |
|---|---|---|---|---|---|---|---|---|
| Absorption rate (min:sec) | 5:06 | 6:20 | 7:08 | 1:40 | 4:04 | 4:40 | 5:21 | 6:35 |
| melting test (sec) | 32 | 45 | 138 | 22 | 32 | 38 | 68 | 95 |
| Migration (%) | 3.95 | 3.29 | 3.54 | 10.56 | 3.75 | 3.46 | 3.40 | 3.41 |

Consequently, comparing Examples 1 to 4 with Comparative Examples 1 and 2 in view of measurement results, it was seen that Examples 1 to 4 using ester plasticizers comprising all components at an appropriate mix ratio exhibited preferable results in view of all physical properties.

Meanwhile, it was seen that Comparative Example 1 using the compound of Formula 2 alone exhibited considerably reduced absorption and fusion times (in this case, gelation was facilitated, and workability and foamability were degraded), but migration became serious.

In addition, it was seen that Comparative Example 2 using the compound of Formula 3 alone exhibited almost no migration, but long absorption and fusion times.

The invention claimed is:

1. A method for preparing an ester composition comprising:
   obtaining hybrid branched, non-hybrid unbranched and non-hybrid branched alkyl-substituted terephthalate compounds through esterification reaction by reacting a terephthalic acid, n-butanol and 2-ethyl hexanol,
   wherein the hybrid branched alkyl-substituted terephthalate compound is present in an amount of 1 to 70% by weight in the ester composition,
   wherein a weight ratio of the non-hybrid unbranched alkyl-substituted terephthalate compound to the non-hybrid branched alkyl-substituted terephthalate compound is 1:99 to 40:60,
   wherein the esterification reaction is carried out in the presence of an acid catalyst, and the acid catalyst comprises at least one selected from paratoluenesulfonic acid, methanesulfonic acid, ethanesulfonic acid, propanesulfonic acid and sulfuric acid, and
   wherein the hybrid branched alkyl-substituted terephthalate compound is represented by Formula 1, the non-hybrid unbranched alkyl-substituted terephthalate compound is represented by Formula 2, and the non-hybrid branched alkyl-substituted terephthalate compound is represented by Formula 3:

[Formula 1]

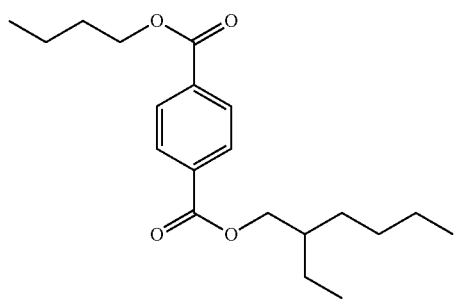

[Formula 2]

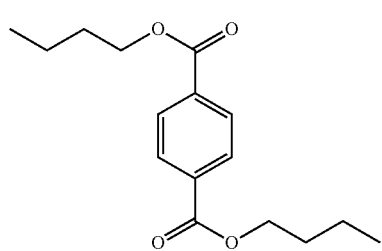

[Formula 3]

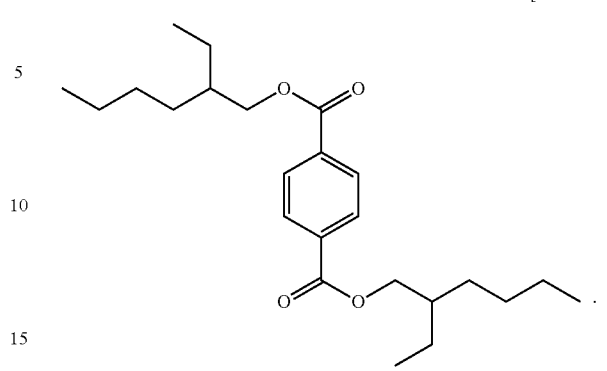

2. The method according to claim 1, wherein the hybrid branched alkyl-substituted terephthalate compound is present in an amount of 1 to 20% by weight.

3. The method according to claim 1, wherein the n-butanol is used in an amount of 1 to 80% by weight with respect to 100% by weight of the n-butanol and 2-ethyl hexanol.

4. The method according to claim 1, wherein the 2-ethyl hexanol is used in an amount of 99 to 20% by weight with respect to 100% by weight of the n-butanol and 2-ethyl hexanol.

5. The method according to claim 1, wherein, an amount of the terephthalic acid used is 10 to 40 mol %, and a sum amount of the n-butanol and the 2-ethyl hexanol used is 90 to 60 mol %, with respect to a sum of moles of the terephthalic acid, the n-butanol and the 2-ethyl hexanol.

6. The method according to claim 1, wherein the hybrid branched alkyl-substituted terephthalate compound is present in an amount of 5 to 50% by weight in the ester composition.

* * * * *